US006827287B2

(12) United States Patent
Elrod et al.

(10) Patent No.: US 6,827,287 B2
(45) Date of Patent: Dec. 7, 2004

(54) HIGH THROUGHPUT METHOD AND APPARATUS FOR INTRODUCING BIOLOGICAL SAMPLES INTO ANALYTICAL INSTRUMENTS

(75) Inventors: Scott A. Elrod, La Honda, CA (US); Steven J. Bank, San Diego, CA (US)

(73) Assignees: Palo Alto Research Center, Incorporated, Palo Alto, CA (US); The Sripps Research Institute, La Jolla, CA (US)

( * ) Notice: Subject to any disclaimer, the term of this patent is extended or adjusted under 35 U.S.C. 154(b) by 0 days.

(21) Appl. No.: 10/329,165

(22) Filed: Dec. 24, 2002

(65) Prior Publication Data

US 2004/0118953 A1 Jun. 24, 2004

(51) Int. Cl.[7] ................................................ B05B 1/08
(52) U.S. Cl. ............................... 239/102.1; 239/102.2; 239/690.1
(58) Field of Search ........................... 239/102.1, 102.2, 239/690, 690.1, 4, 67, 68, 69; 128/200.14, 200.16; 347/9, 20, 47, 68

(56) References Cited

U.S. PATENT DOCUMENTS

| | | | |
|---|---|---|---|
| 4,751,529 A | | 6/1988 | Elrod et al. |
| 4,782,350 A | * | 11/1988 | Smith et al. ................... 347/46 |
| 4,959,674 A | * | 9/1990 | Khri-Yakub et al. .......... 347/46 |
| 5,191,354 A | * | 3/1993 | Quate ........................... 347/94 |
| 5,194,880 A | | 3/1993 | Elrod et al. |
| 5,565,113 A | | 10/1996 | Hadimioglu et al. |
| 5,591,490 A | * | 1/1997 | Quate .......................... 427/457 |
| 5,669,971 A | * | 9/1997 | Bok et al. .................... 118/300 |

(List continued on next page.)

FOREIGN PATENT DOCUMENTS

| | | | |
|---|---|---|---|
| JP | 359111053 A | * | 6/1984 |
| JP | 02002107344 A | * | 4/2002 |

OTHER PUBLICATIONS

S.A. Elrod, et al., *Nozzleless Droplet Formation with Focused Acoustic Beams*, J. Appl. Phys., vol. 65 No. 9, May 1, 1989.

Primary Examiner—William E. Tapolcai
Assistant Examiner—Mohammad M. Ali
(74) Attorney, Agent, or Firm—Fay, Sharpe, Fagan, Minnich & McKee, LLP

(57) ABSTRACT

Provided is a system for delivering a liquid sample to an inlet of an analytical instrument. Included is an acoustic ejector driven by a drive system that generates drive signals provided to the ejector. The drive signals are generated with a pulse width sufficient to eject at least a portion of the liquid sample. A reservoir provided for holding the liquid sample is in operational arrangement with the acoustic ejector. A liquid sample voltage source is located within the reservoir, and the liquid sample voltage source is designed to provide a charge to the liquid sample. An analytical instrument voltage source is in operational arrangement with the analytical instrument and is designed to provide a voltage bias between the reservoir and the analytical instrument.

In another aspect of the invention, provided is a method for delivering a liquid sample to an inlet of an analytical instrument. The method includes generating an acoustic drive signal, with a pulse width sufficient to eject at least a portion of the liquid sample below a short pulse limit. The drive signal is delivered to an acoustic ejector whereby the acoustic ejector generates an acoustic wave. The acoustic wave is directed into a reservoir holding the liquid sample, wherein the acoustic wave is focused substantially at a surface of the liquid sample. This design results in the emitting of at least a portion of the liquid sample.

27 Claims, 8 Drawing Sheets

U.S. PATENT DOCUMENTS

| | | | |
|---|---|---|---|
| 5,877,495 A * | 3/1999 | Takada et al. | 250/288 |
| 6,134,291 A | 10/2000 | Roy et al. | |
| 6,188,065 B1 * | 2/2001 | Takada et al. | 250/288 |
| 6,232,114 B1 | 5/2001 | Coassin et al. | |
| 6,335,525 B1 * | 1/2002 | Takada et al. | 250/288 |
| 6,405,934 B1 * | 6/2002 | Hess et al. | 239/4 |
| 6,416,164 B1 | 7/2002 | Stearns et al. | |
| 6,548,308 B2 * | 4/2003 | Ellson et al. | 436/180 |
| 6,603,118 B2 * | 8/2003 | Ellson et al. | 250/288 |
| 6,622,720 B2 * | 9/2003 | Hadimioglu | 128/200.16 |
| 6,666,541 B2 * | 12/2003 | Ellson et al. | 347/46 |
| 2002/0073989 A1 | 6/2002 | Hadimioglu | |
| 2002/0073990 A1 | 6/2002 | Noolandi et al. | |
| 2002/0077369 A1 | 6/2002 | Noolandi et al. | |
| 2002/0109084 A1 | 8/2002 | Ellson et al. | |

* cited by examiner

HIGH THROUGHPUT METHOD AND APPARATUS FOR INTRODUCING BIOLOGICAL SAMPLES INTO ANALYTICAL INSTRUMENTS

BACKGROUND OF THE INVENTION

The present application is directed to droplet ejection, and more specifically, to the generation and transmission of droplets to analytical instruments such as mass spectrometers.

Mass spectrometers are an analytical tool concerned with the separation of molecular (and atomic) species according to their mass and charge. More particularly, it is an analytical tool used for measuring the molecular weight (MW) of a sample. For large samples such as biomolecules (e.g., analyte molecules), molecular weights can be measured within an accuracy of 0.01% of the total molecular weight of the sample, i.e., within 4 Daltons (Da) or atomic mass units (amu) error for a sample of 40,000 Da. More commonly, the accuracy is about 0.05% or 20 Da with a good measurement and multiple charge states present. This is sufficient to allow minor mass changes to be detected, e.g., the substitution of one amino acid for another. Often, however, there are substitutions for amino acids that do not significantly alter the mass (i.e., isoleucine and leucine have the same mass), these substitutions may pose problems for any mass spectrometer. For small organic molecules, the molecular weight can be measured to within an accuracy usually sufficient to confirm the molecular formula of a compound. To achieve such measurements, a mass spectrometer of sufficient resolution will of course be required.

Mass spectrometers are particularly useful for analyzing the products of chemical reactions, since they can identify specific products by their mass signature. However, large complexes, such as protein-ligand interactions have been difficult to detect using conventional mass spectrometry methods. This is in part due to the fact the introduction and charging of the sample is a relatively violent process, which tends to break up larger molecules into fragments. Fortunately, new sample introduction techniques have been developed, such as electrospray ionization (ESI), which are much less violent, making it possible to now detect protein ligand complexes directly in mass spectrometers. Such mass spectrometers are ESI-quadrupole mass spectrometers, one in particular being ESI time-of-flight of mass spectrometers (ESI-TOF mass spectrometers).

There are numerous types of mass spectrometers, in addition to those known as time-of-flight. However, the basic components are similar. As shown in FIG. 1, mass spectrometer 10 can be divided into three fundamental parts. First, an ion source 12 ionizes the molecules of interest, then a mass analyzer 14 differentiates the ions according to their mass-to-charge ratio, and finally a detector 16 measures an ion beam current. Each of these elements can take many forms and are combined to produce a wide variety of mass spectrometers with specialized characteristics.

The analyzer and detector of the mass spectrometer, and often the ionization source, are maintained under high vacuum 17 to provide the ions a path to travel from one end of the instrument to the other without hindrance from other molecules. The entire operation of the mass spectrometer, and often the sample introduction process, is under a system controller 18.

As may be apparent from the foregoing, an important aspect of mass spectrometry is sample introduction into the instrument 10. The sample inlet 19 is the interface between the sample and the mass spectrometer. One approach is to place a sample on a probe which is then inserted, usually through a vacuum lock, into the ionization region of the mass spectrometer 10. The sample can then be heated to facilitate thermal desorption or undergo any number of high-energy desorption processes used to achieve vaporization and ionization.

Capillary infusion is often used because it can efficiently introduce small quantities of a sample into a mass spectrometer without destroying the vacuum. Capillary columns are routinely used to interface the ionization source of a mass spectrometer with other separation techniques, including, but not limited to, gas chromatography, liquid chromatography (LC), high pressure liquid chromatography (HPLC) or capillary electrophoresis (CE).

Up until twenty years ago, practical techniques for interfacing liquid chromatography (LC) with available ionization techniques were not available. A major problem prohibiting this interface was getting the sample stream from the liquid chromatographic process into the mass spectrometer without losing vacuum while also ionizing the sample. However, new ionization techniques, such as the previously mentioned electrospray ionization, allow liquid chromatography/mass spectrometry processes to be routinely performed. One configuration of a liquid chromatography/mass spectrometry design 20 is shown in FIG. 2. More particularly, a pump 22 moves a sample liquid to chromatographic separation columns 24 wherein the liquid sample is separated into a series of components. The liquid sample is then sent to a capillary spray nozzle or needle 26, and electrospray 28 ionization processes 28 are performed 28. The ionized sample is then introduced to mass analyzer 30, and detected by detector 32 for generation of output signals 34.

As previously noted, the ionization source in this example is an electrospray ionization system. A more detailed view of such a system is shown as electrospray configuration 40 of FIG. 3. In this design, a liquid sample 42, which may be provided from the liquid chromatography process of FIG. 2 moves through a metal capillary or needle 44, which has an open end with a sharply pointed tip, such as the end of a syringe. This tip is attached to a voltage supply 45 of between approximately 1.5 kv to 4 kv, depending upon the implementation. The end of the tip faces a counterelectrode plate or cylinder electrode 46 held at a voltage lower than the tip voltage to generate a voltage gradient. As the voltage in the liquid is applied, the liquid becomes charged, generating a force sufficient to expel the liquid from the capillary tip. As the liquid sample 42 pushes from the tip, a shape described as a Taylor cone is developed. At the very end of the cone, the droplets push away from one another into a fine spray 48, at times called a plume. It is to be appreciated that a capillary LC process uses pump pressure to expel the fluid.

Depending on the electric field used, the charges may be positive or negative. The droplets may contain both solvent molecules, as well as analyte (sample) molecules and may be less than 10 micrometers across. The droplets move across the electric field, and with the assistance of a flow of $N_2$ gas, provided by gas inlet 50, neutral solvent molecules are evaporated from the droplets. As the droplets become smaller, and the total charge on the droplets stays the same, so the concentration of charge increases. Eventually, at what is known as the Rayleigh limit, Coulombic repulsion overcomes the droplet surface tension and the droplet explodes. The Coulombic explosion forms a series of smaller, lower-charged droplets. This process of shrinking followed by explosion is repeated, until eventually the analyte (sample)

molecule is stripped of solvent molecules, and is left as a charged ion. These ions are then moved through capillary 52, which is in a differently pumped region 54. A skimmer 56 may be provided to further refine the sample.

A major instrumental challenge with electrospray ionization is the interface between the ion source (which may be at atmospheric pressure) and the mass spectrometer (at a high vacuum, one example value may be about $10^{-6}$ torr; it is to be appreciated however that this value is instrument dependent). This problem is addressed by the use of a pinhole aperture 58 around 10–100 micrometers. In this design, the created ions are drifted (with the help of the electric field) towards the aperture. The emitted drops are then, as previously noted, analyzed in the analysis section and then provided to a detector for generation of output signals.

It is to be appreciated that in addition to the described electrospray technique, other ionization designs are known, such a nanospray technology. This process is similar to electrospray technology, but uses a smaller capillary, and requires less sample solution, i.e., it is a low flow rate version of electrospray ionization.

Thus, as shown above, use of electrospray ionization and nanospray ionization, provides increased uses of mass spectrometry. Particularly, these techniques permit for the integration of separation functions, such as liquid chromatography type technology with the mass spectrometry.

Unfortunately, electrospray and/or nanospray sample introduction remains relatively slow, since it relies on the plumbing of fluids through small capillary tubes prior to droplet generation with a high electric field. For operations which would benefit from high throughput, such as drug screening and others, it is desirable to have sample introduction techniques which are substantially faster.

Another drawback of the techniques described is the potential for contamination. Specifically, since the sample is required to pass through substantial amounts of tubing and come into contact with a number of distinct surfaces, the potential for contamination of the sample exists.

Further, in areas such as combinatorial chemistry and others, the sample fluids are contained within wells of a well-plate. Often it is desired to review the reaction of byproducts resulting from the combination of the fluids in the wells. Presently it is necessary to process the fluids through the capillary tubing required by existing liquid chromatography/mass spectrometry configurations. Thus a drawback exists in that it is necessary to remove the fluids from the well of the well-plate prior to providing the sample fluid to the mass spectrometer. One example of providing a sample from a well-plate to a mass spectrometer is described in U.S. Patent Application 2002/0109084 A1, entitled Acoustic Sample Introduction For Mass Spectrometric Analysis, published Aug. 15, 2002, filed February 14, 2001, hereby incorporated in its entirety by reference.

BRIEF DESCRIPTION OF THE INVENTION

Provided is a system for delivering a liquid sample to an inlet of an analytical instrument. Included is an acoustic ejector driven by a drive system that generates drive signals provided to the ejector. The drive signals are generated with a pulse width sufficient to eject at least a portion of the liquid sample. A reservoir provided for holding the liquid sample is in operational arrangement with the acoustic ejector. A liquid sample voltage source is located within the reservoir, and the liquid sample voltage source is designed to provide a charge to the liquid sample. An analytical instrument voltage source is in operational arrangement with the analytical instrument and is designed to provide a voltage bias between the reservoir and the analytical instrument.

In another aspect of the invention, provided is a method for delivering a liquid sample to an inlet of an analytical instrument. The method includes generating an acoustic drive signal, with a pulse width sufficient to eject at least a portion of the liquid sample below a short pulse limit. The drive signal is delivered to an acoustic ejector whereby the acoustic ejector generates an acoustic wave. The acoustic wave is directed into a reservoir holding the liquid sample, wherein the acoustic wave is focused substantially at a surface of the liquid sample. This design results in the emitting of at least a portion of the liquid sample.

DETAILED DESCRIPTION OF THE PREFERRED EMBODIMENT

Figure 1:
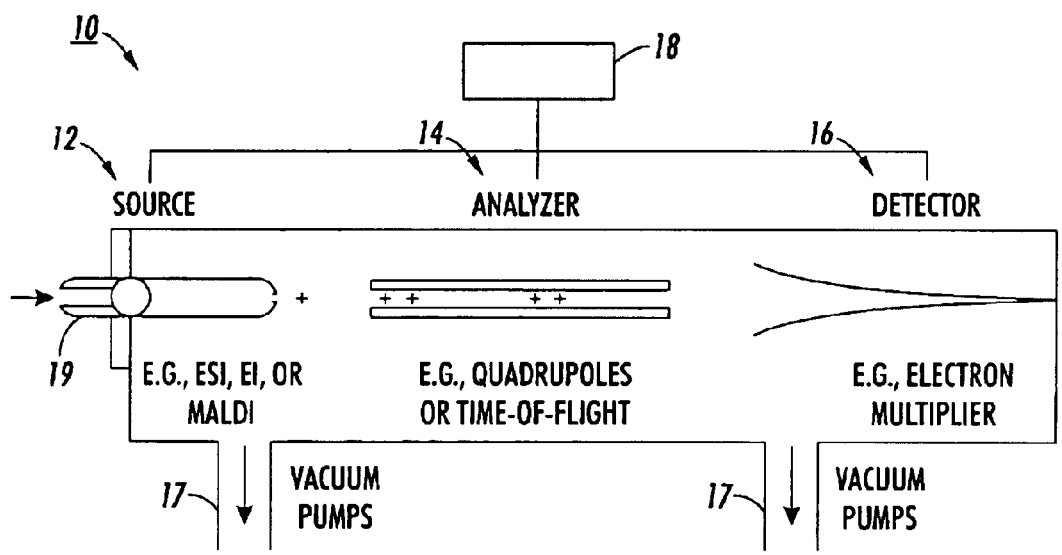
FIG. 1 shows a general outline of a mass spectrometer, parts of which may be used in the present system.
Figure 2:
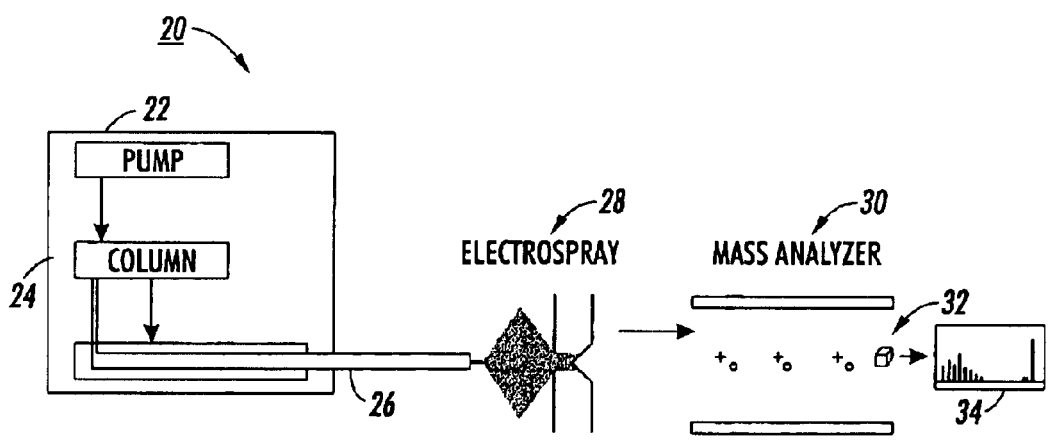
FIG. 2 is a prior art configuration of a liquid chromatographic system implemented with a mass spectrometer.
Figure 3:
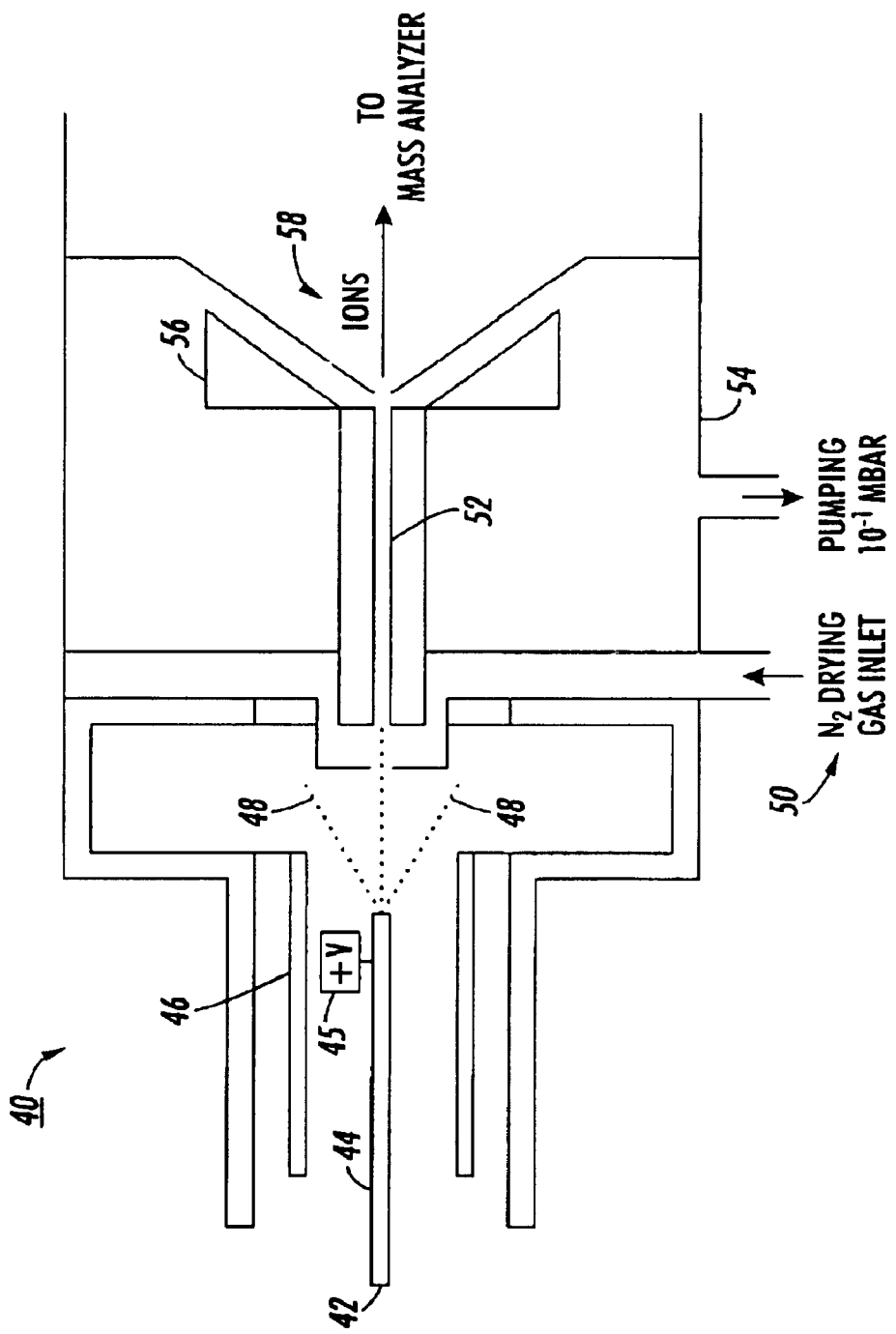
FIG. 3 provides a more detailed view of an electrospray ionization configuration.

FIGS. 1–3 discuss providing a sample to a mass spectrometer, where a sample is introduced to the mass spectrometer, where the introduction may be by an electrospray technique (see FIG. 2) or other introduction processes. The sample is in one instance provided via a liquid chromatographic process.

Figure 4A:
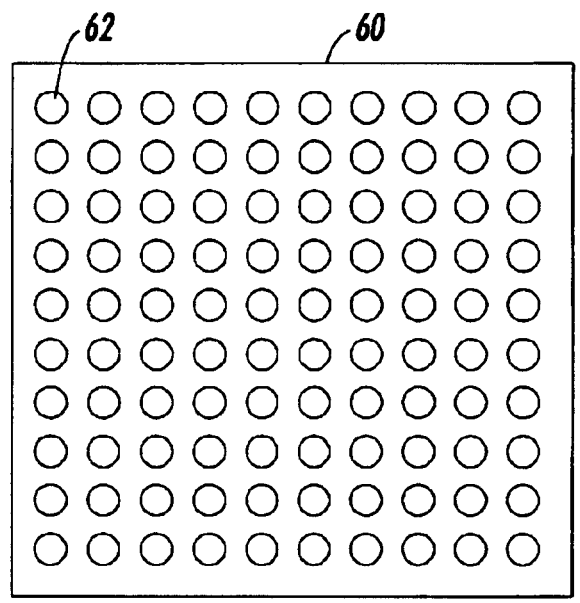
FIG. 4A is a planar view of a multi-well-plate which may be used in connection with concepts of the present application.
Figure 4B:
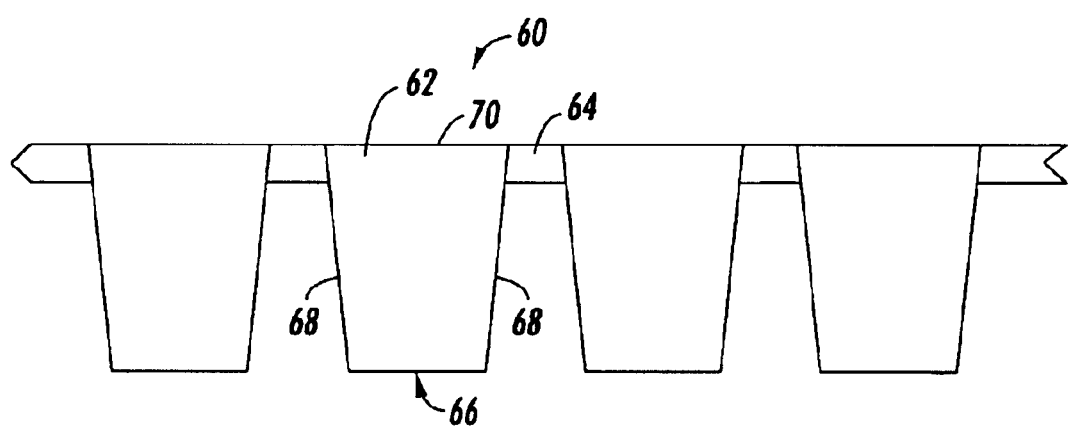
FIG. 4B provides a portional cross-sectional view of FIG. 4A.

Turning to FIG. 4A depicted is a planar view of a multi-well plate 10 which may be used in connection with concepts of the present application. It is understood that well-plate 60 represents well-plates having any number of wells (i.e., reservoirs) 12. FIG. 4B provides a portional cross-sectional view of well-plate 60. As shown in the cross-sectional portional view, the plurality of reservoirs 62 are spaced within the well plate, where the reservoirs 62 are connected within the overall well-plate via an upper interconnection surface 64. The reservoirs 62 which include a bottom surface 66, side walls 68 and a top aperture 70, are spaced from each other.

Multi-well plates which may be used in connection with concepts of the present application can have any number of wells in any well arrangement, on any multi-well plate format or footprint. Typically, the wells are arranged in two-dimensional linear arrays such as shown in FIG. 4A, and usually have between 96 and 384 wells. However, it is to be appreciated that well plates with a larger number of wells such as 1536, 3456, and 9600, as well as other well plate sizes, may be used.

Well volumes typically vary from 500 nanoliters or less to over 200 microliters, depending on well depth and cross-sectional area. Wells can be made in any cross-sectional shape (in plan view), including square, round and hexagonal, and in combinations thereof. Wells can be made in any cross-sectional shape (in vertical view), including shear vertical walls with flat or round bottoms, conical walls with flat or round bottom, and curved vertical walls with flat or round bottoms and combinations thereof.

The materials for manufacturing the well plates are typically polymeric, since these materials lend themselves to mass manufacturing techniques. Polymeric materials can particularly facilitate plate manufacture by molding methods known in the art and developed in the future. One particular type of multi-well plate is a microtiter plate.

It is to be appreciated that, while the well-plate described in FIG. 4B, has unobstructed access to the side walls, other embodiments of the present application do not need access to the side-walls, and well plates having bottom support beams or components may also be used.

Figure 5:
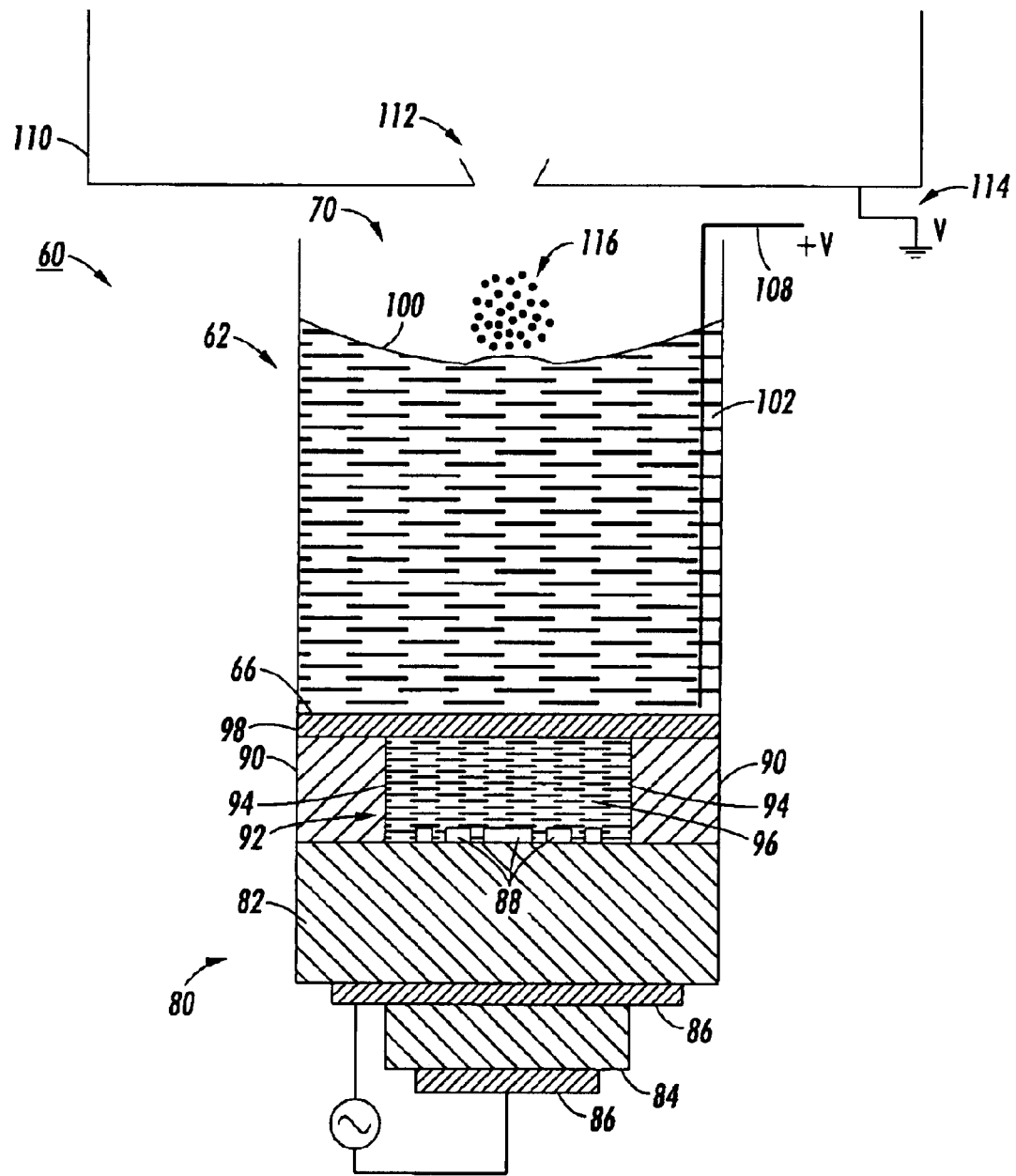
FIG. 5 depicts a first embodiment in which concepts of the present application may be implemented.

FIG. 5 depicts a first embodiment in which the concepts of the present application may be implemented. Shown in cross-section is a droplet emitter 80 in operational association with a well 62 of well-plate 60. It is to be understood the described droplet emitter is but one of various acoustic focused emitter designs which may be implemented in accordance with the concepts of the present application. More particularly, the specific placement of various components may be rearranged, and, as is well-known in the art, may still operate as an acoustic emitter. It is intended that the description be understood to also include these other arrangements.

Droplet emitter 80 has a base substrate 82 with a transducer 84 interposed between two electrodes 86 on one surface and an acoustic lens 88 on an opposite surface. Attached to the same side of the base substrate 82 as the acoustic lens 88 is a top support 90 with a liquid cell 92 defined by sidewalls 94, which holds a low attenuation liquid 96. Supported by the top support 90 is an acoustically thin capping/acoustic coupling structure 98 which forms the top surface of the liquid cell 92 and seals in the low attenuation liquid 96. It is to be appreciated that capping/acoustic coupling structure 98 does not need to be permanently physically attached to the reservoir/well 62. Rather, capping/acoustic coupling structure 98 may at times only be acoustically coupled to the bottom of well 62. In these situations the capping/acoustic coupling structure 98 may be designed with a conformable polymer and/or an acoustic coupling material provided between capping/acoustic coupling structure 98 and well bottom 66, such as grease, or other appropriate substance.

Droplet emitter 80 is located over, and acoustically coupled to, bottom surface 66 of well 62 of well-plate 60. As shown in FIG. 5, the transducer 84, acoustic lens 88, and aperture 70 of well 62 are all axially aligned such that an acoustic wave produced by the transducer 84 will be focussed by its aligned acoustic lens 88: at approximately the free surface 100 of the emission fluid 102.

To generate an acoustic beam which focuses at the fluid surface 100, a number of different acoustic lens types may be used dependant upon the ratio of aperture opening to height of the fluid contained in the well or reservoir. Particularly, as discussed by Elrod et al. (1989) J. Appl. Phys. 65 (9): 3441–3447, and as used in U.S. Pat. No. 6,416,164 to Stearns et al. (issued Jul. 9, 2002), both hereby incorporated by reference, when using lenses having an F-number equal to 1, the resulting drop size will be substantially equal in size to the focused beam. Using a higher F-number lens, i.e., a more weakly focused lens permits the projection of a focal point farther into a column of fluid where either the aperture or the plane of entry of the acoustic energy is limited in size. Thus, concepts of the present application may be implemented with both tightly focused beams having an F-number of 1 and more weakly focused lenses having F-numbers greater than 1, depending on the configuration of the well or reservoir.

Also noted in the Elrod material is that droplet ejection stability is sensitive to the width of the acoustic pulse. For tone bursts, there is a certain minimum pulse width $t_{min}$ below which droplet formation is considerably less stable, and is accompanied by a mist which emanates from the acoustic focus. It was submitted that the mist results from the parametric generation of capillary waves in the focal spot. Aerosol formation from capillary waves is understood, and one would expect it to occur for acoustic intensities above a certain threshold value. Threshold energy is found to vary only slightly with acoustic pulse width, hence the acoustic intensity must increase as the pulse width is reduced. Droplets generated from capillary waves were noted to have a mean diameter given by:

$$D = 0.34(8\pi T/\rho_b f^2)^{1/3},$$

where T is the surface tension of the fluid, ρb is the bulk liquid density of the fluid and f is the acoustic frequency.

At 5 MHz, this yields 1.4 μm. At 5 MHz, the minimum pulse width ($t_{min}$) is about 20 μsec, below which capillary mist droplets are generated. Minimum pulse width scales approximately as $f^{-1}$.

Figure 6A:
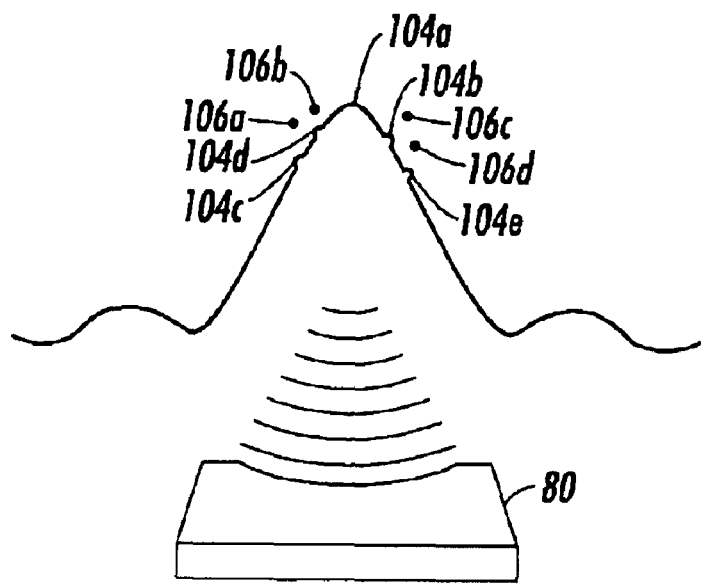
FIG. 6A shows ejection of droplets using capillary action.

When generating capillary wave-driven droplets, and as shown in FIG. 6A, a principal mound 104a does not receive enough energy to eject a droplet. Instead, the top surface of the principal mound, and more particularly at the tip of the principal mound, becomes covered by capillary wave crests 104b, 104c, 104d, 104e (It is noted FIG. 6A is not to scale as the capillary waves superimposed on top of the principal mound 104a are in the range of 1 μm across and the principal mound is about 300 um across.) These wave crests eject a mist corresponding to droplets 106a, 106b, 106c, 106d. In order to generate capillary action droplets instead of focused, single ejection droplets, each ejector transducer provides shorter pulse widths at a higher peak power. Example pulse widths are on the order of 5 microseconds or less for an acoustic frequency of 5 MHz.

One advantage of using capillary action is that lower frequencies can be used to create smaller droplets. The diameter of capillary generated droplets is similar in magnitude to the wavelength of capillary waves. The wavelength of capillary waves can be determined from the equation: wavelength=$[2*\pi*T/(\rho*f^2)]^{(1/3)}$ wherein T is the surface tension of the fluid, ρ is the density of the fluid and f is the acoustic frequency output of the transducer. This equation and a more detailed explanation are provided on page 328 of Eisenmenger, Acoustica, 1959 which is hereby incorporated by reference. At typical densities and surface tensions, frequencies of 10 Megahertz (MHz) generate a capillary wavelength of 1.5 micrometers and a frequency of 1 MHz generates a capillary wavelength of 6.8 micrometers. Thus it is possible to generate micrometer diameter droplets at RF frequencies much smaller than the bulk waves used to generate "conventional" AIP droplets which are in the range of 100–300 MHz. An example of a conventionally described acoustic ejector, used for ejection of ink and other major drops is U.S. Pat. No. 5,565,113 to Hadimioglu, entitled Lithographically Defined Ejection Units, hereby incorporated by reference.

In capillary wave droplet systems, the lower frequencies used allows more flexibility in materials and tolerances used to fabricate transducers and acoustic lenses used to form the array of droplet sources. For example, plastics are not as lossy at the lower frequencies. The lower loss levels would allow relatively inexpensive molded spherical lenses to be used as acoustic lenses. Use of capillary waves to generate a mist of droplets is discussed in commonly owned U.S. application Ser. No. 09/739,988, entitled, "Using Capillary Wave Driven Droplets To Deliver A Pharmaceutical Product," hereby incorporated by reference.

Using this information, and returning attention to FIG. 5, further discussion of the present embodiment is set forth. An electrode 108 having a positive voltage of approximately between 3.5 kv and 5 kv, depending on the particular implementation, is located within the fluid 102 of well 62. Analytical instrument 110, which in one embodiment is a mass spectrometer, is located opposite the aperture 70 of well 62, where an inlet 112 of mass spectrometer 110 is aligned substantially across from the point of mist/droplet ejection from aperture 70. It is to be appreciated an analytical instrument 110 may be any of the numerous mass spectrometers, different types of accelerators or any other instrument which would benefit from the concepts of the present application.

A counter-electrode 114 is associated with the mass spectrometer. Use of electrodes 108 and 114 provide a voltage between fluid 102 and inlet 112 of mass spectrometer 110. The operation of the present system is intended to permit direct ejection of fluid 102 from well 62, in order to replace the emitter tip or syringe used in electrospray ionization processes.

Emitter 80, in one embodiment, is operated to launch mist or spray of droplets 116 (i.e., made up of droplets such as 106a–106d) during the time a voltage bias (108–114) exists between the fluid 102 and aperture 112 of mass spectrometer 10. In other embodiments, emitter 80 may be operated to generate drops in accordance with "conventional" AIP droplets as described in the previously-cited Hadimioglu patent (U.S. Pat. No. 5,565,113). The voltage bias produces an electric field used to accelerate the drops towards the mass spectrometer 110.

To generate the mist 116, emitter 80 is operated below the short pulse limit $t_{(min)}$. This short pulse limit imparts acoustic energy sufficient to create a rising cone, created by the acoustic radiation pressure, on the free surface 100 of liquid 102. This results in the generation of capillary waves from which are emitted the small droplets, wherein thousands of these droplets may be generated per acoustic pulse.

In order to supply energy to create the capillary wave action, but not generate a large or major drop, ejector 80 is operated below the short pulse limit, which is obtained by maintaining the pulse width sufficiently short in correspondence to the frequency of operation. Particularly, for a system operating at a frequency of 5 MHz, whereby a 300 micron primary drop could be ejected with a longer pulse width, the pulse width would be at or below approximately 5 microseconds to be below the short pulse limit. At this pulse width limit, there is not sufficient momentum in the acoustic pulse to cause a large droplet to break away from the free surface. It is noted that the short pulse limit scales with the drive frequency. Particularly, as the drive frequency is increased, the pulse width needs to become shorter to be under the short pulse limit.

Figure 6B:
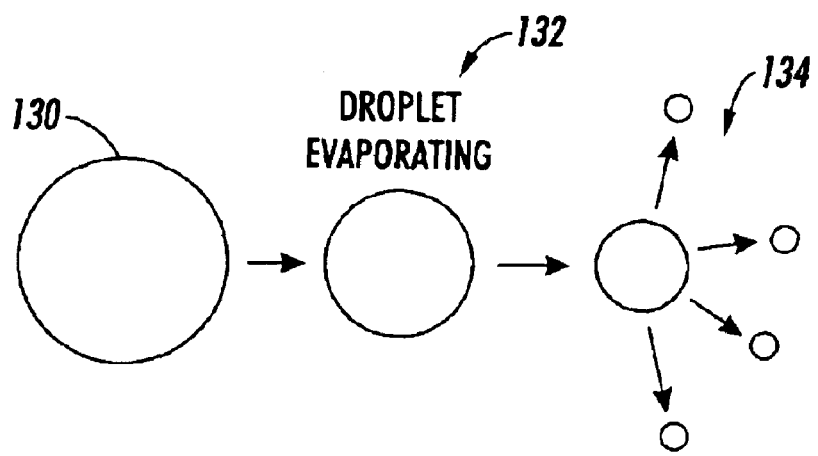
FIG. 6B shows droplet evaporation and spontaneous fission of a droplet from the mist of droplets.

Upon ejection, and as shown in FIG. 6B, a droplet 130 which represents any one of the droplets of the mist of droplets 116 become smaller 132 due to droplet evaporation. The droplet evaporation may occur naturally or the system may include an evaporation arrangement such as known in the art. This droplet will have a sufficient charge so as to undergo a spontaneous fission, creating yet smaller droplets 134 as it propagates across the electric field. This spontaneous fission is repeated through the droplets' travel. It is worth noting that charging of the fluid is enhanced at the peaks of the capillary waves. Such enhancement occurs by the e-field enhancement at these peaks.

In view of the design of the described system and its size, there is the possibility that use of a voltage sufficiently large to ensure the spontaneous fission may also risk the generation or pulling of larger than desired amounts of fluid due to electrostatic force. To address this issue, charging of the fluid surface may be accomplished via a pulsing voltage. Particularly, a short high-voltage pulse is generated substantially only during the time the acoustic waves are at the fluid surface. By controlling voltage source 108 to produce short pulses, there will not be sufficient momentum to generate a main or large drop. Therefore, by this embodiment both the acoustics and voltages are constrained to a narrow time window for each mist/spray ejection.

As previously mentioned, operating an appropriate acoustic emitter at 5 MHz, will cause a primary drop of approximately 300 microns to be generated. However, by ensuring the pulse width is below the short pulse limit, mist/spray droplets on the order of 1 micron in diameter or smaller may be generated. While, for some operations 1 micron may be sufficiently sized, for other implementations the 1 micron droplets may be too large. Thus, charging of the fluid surface by the application of voltage 108 is used to assist in the creation of the spontaneous fission for generation of smaller sized mist/spray droplets.

Figure 7:
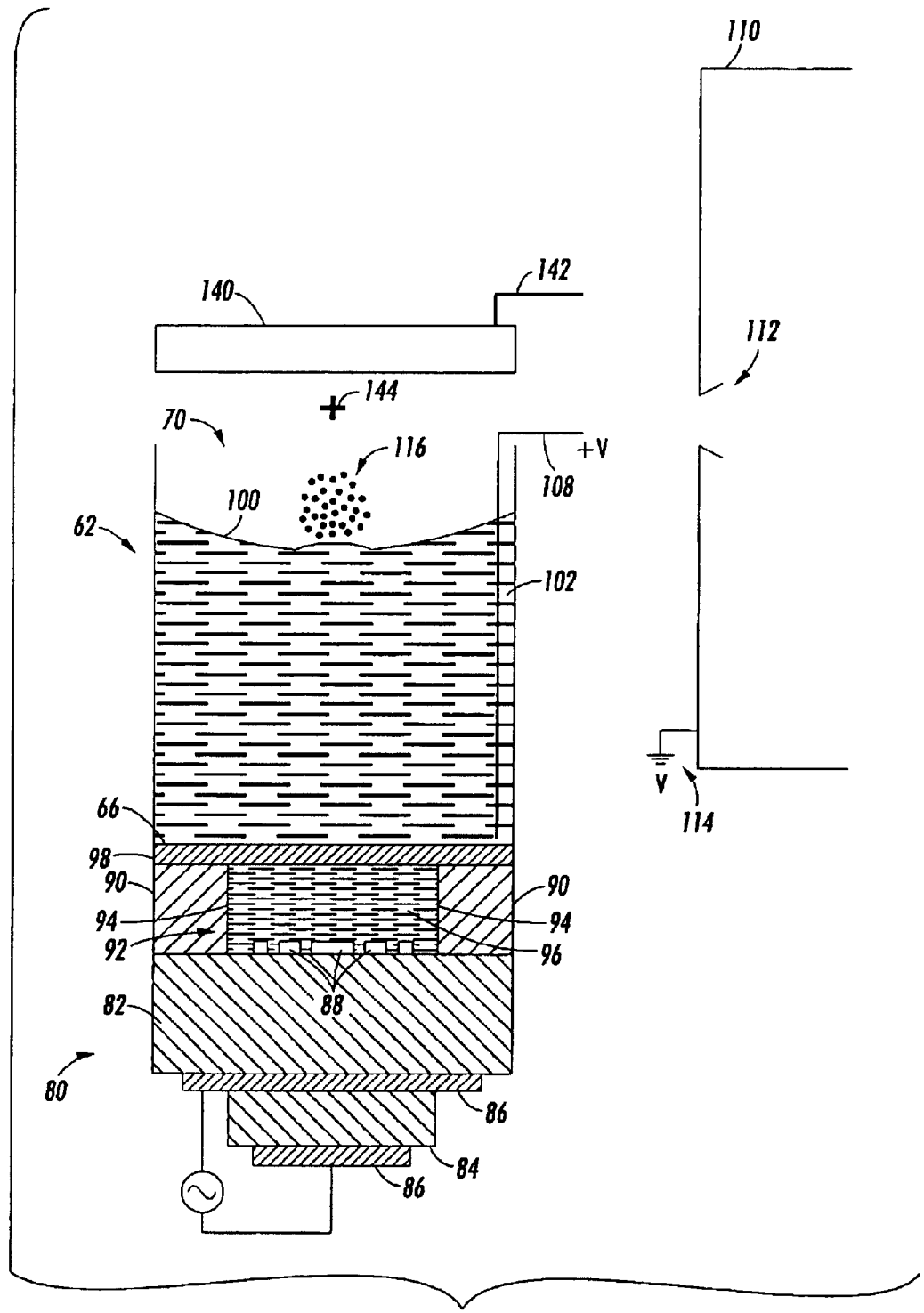
FIG. 7 illustrates another embodiment of concepts presented in the present application.

Turning to FIG. 7, illustrated is another embodiment of concepts presented the present application, where axis of the mass spectrometer 110 (or other analytical instrument) is substantially orthogonal to the mist ejection path as it is ejected from the aperture of the reservoir. This arrangement means the droplets of mist 116 cannot be moved directly into inlet 112. To address this issue, a charge plate 140 is provided in the path of mist 116. Charge plate 140 includes a voltage source 142 which selectively generates a voltage (such as 5 k volts). Upon ejection, the mist droplets 116 are accelerated towards plate 140 due to the voltage path generated between voltage source 108 (at approximately 5 Kv) and voltage source 142 (which at this initial period will be less than the voltage applied to the fluid. At a prescribed time voltage source 142 is turned off and voltage source 114 of mass spectrometer 110 is turned on up (to around 5 Kv). In one embodiment the switching on of voltage source 142 and the placing of voltage source 114 to common will occur when the droplets are at substantially a midpoint 144, within the path, and generally aligned to the aperture 112 of mass spectrometer 110. This operation causes flight diversion of the mist droplets, so they are then accelerated to inlet 112. This embodiment, teaches that ejector 80 and mass spectrometer 110 configuration does not require direct movement of mist 116 from ejector 80 to inlet 112.

Figure 8:
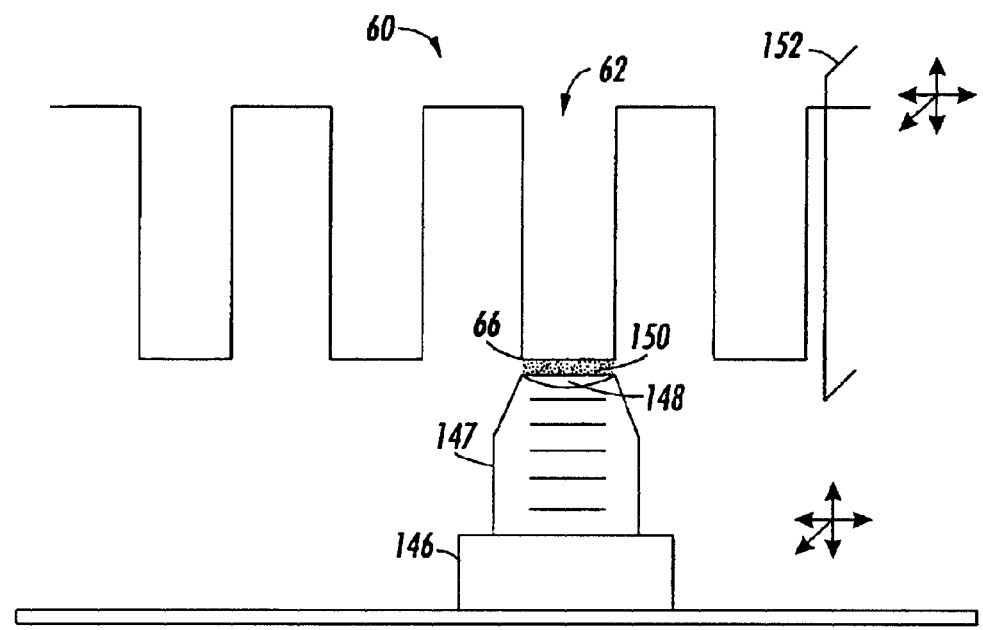
FIG. 8 illustrates a further embodiment of the present application where movement of the acoustic ejector and/or the well-plates are identified.

Turning to FIG. 8, as previously noted, the present application may work in conjunction with a well-plate 60 having a plurality of wells 62. In this system, a transport 146 is used to move ejector 147 in the X, Y and Z directions to operationally engage a selected well of the well-plate. By this design, once a mist has been emitted from a selected well, ejector 147 may be moved to another well to perform a next ejection operation. It is to be appreciated that ejector 147 employs a coupling design which is different in its geometry than that shown in the previous figures. In this configuration, lens 148 focuses in a single coupling fluid 150, such as water or other appropriate substance into the bottom 66 of the well 62.

As also shown alternatively in FIG. 8, ejector 147 may be stationary, and well-plate 60 may be associated with a transport 152 designed for moving well-plate 60 in the X, Y and Z directions. By this operation, it is well-plate 60 which is moved into an appropriate manner relative to ejector 147. This embodiment may be implemented both in the designs of FIGS. 6 and 7.

Figure 9:
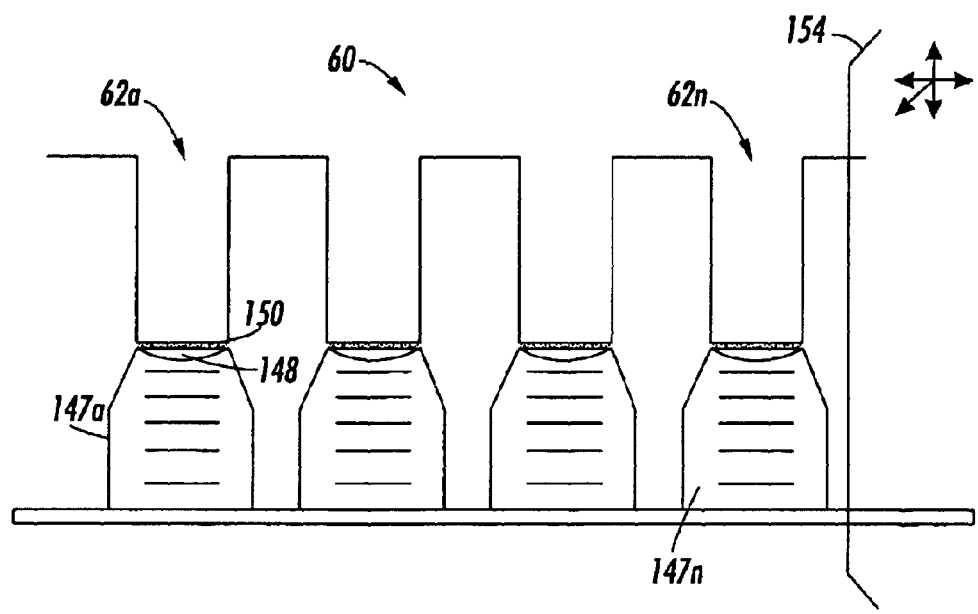
FIG. 9 illustrates an embodiment of the present invention using a plurality of ejectors in operational arrangement with a plurality of wells of the well-plate.
Figure 10:
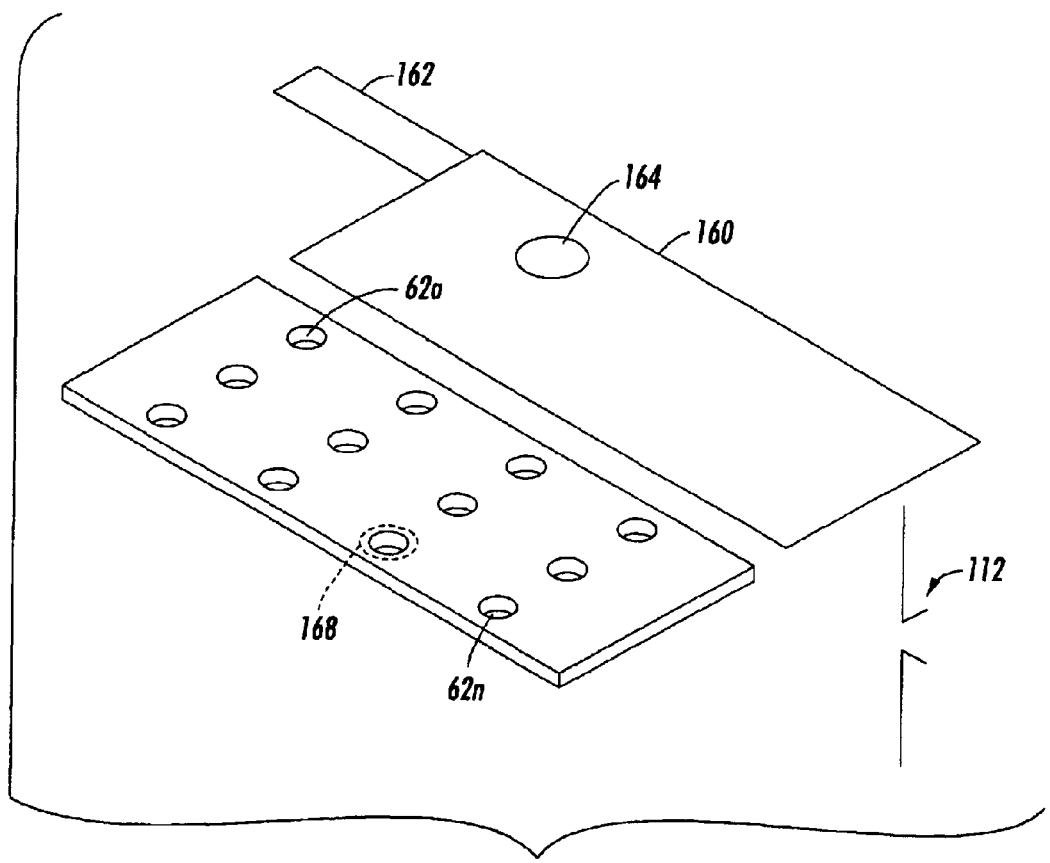
FIG. 10 sets forth a system to avoid contamination between wells of the well-plate.

Turning to FIG. 9, illustrated is a further embodiment wherein a plurality of ejectors 147a–147n are in operational arrangement with wells 62a–62n of the well-plate 60. In this design the multiple ejectors 147a–147n and wells 62a–62n are moved together by transport 154. The movement places wells and corresponding ejectors at appropriate positions, such that when a mist is ejected it will be received at an inlet. It is noted that as a further refinement, a plurality of mass spectrometer 110 (not shown) may be arranged so that drops from wells may be directed to different mass spectrometers during substantially the same time. This embodiment may be implemented both in the designs of FIGS. 6 and 7.

It is appreciated that prevention of contamination of the samples in individual wells 62 of well-plate 60 is a valuable consideration. Particularly, the samples may commonly be valuable fluids whose contamination would result in an economic loss. Further, contamination of the fluid will provide unusable results from the mass spectroscopy procedures. To avoid contamination, various safety mechanisms may be implemented.

In a simple design, a protection plate 160 may be provided on a transport system 162. Protection plate 160 will have an opening 164. When a particular well, such as well 62a of well-plate 60 is going to have a mist ejected, protection plate 160 will be moved whereby opening 164 is placed over well 62a until the ejection process is complete. By this design, the other wells of well-plate 60 are covered and will not be contaminated by the droplets emitting from well 62a. It is understood that in some instances protection plate 160 may be sufficiently sized and overlap the well-plate 60 such that placement of opening 164 at any of the wells will cover the remaining unused wells. It is to be understood in some embodiments, when the fluid is being directed to an inlet 112, those wells behind a well from which fluid is being emitted do not need to be covered. For example, if well 62n is operational, then wells such as 62a do not need to be covered. Also, protection plate 160 may be designed as separately controlled cover portions to minimize the size of the protection plate.

An alternative embodiment provides controllable covers fitted over each individual well whereby upon operation, the cover would open and then close. Such a structure may be implemented, for example, using micro-electromechanical-structure (MEMS) covers such as 168. Particularly a MEMS cover 168 may open for a short time interval allowing droplets to be ejected and remain closed during other periods. In one embodiment, the cover, whether a large area cover or a MEMS cover, will be electronically controlled such that the ejection of droplets causes the cover or protection plate to automatically retract out of the path of the ejected droplets. Such electronic control may be achieved by synchronizing a cover or protection plate control with the electrical impulse driving of the transducers.

Thus, in addition to other teachings, the present application teaches a system which includes an analytical device having an ionization chamber for analyzing an analyte molecule. This system also has a reservoir holding a fluid sample comprised of the analyte molecule, an ejector comprising an acoustic radiation generator for generating acoustic radiation, focusing means for focusing the acoustic radiation at a focal point near the surface of the fluid sample, a means for positioning the ejector in acoustic coupling relationship to the reservoir to eject a droplet of the fluid sample into the ionization chamber.

It is understood that the concepts set forth above may be accomplished through the use of either of the ejector types described. Further, the ejected fluid may be any of numerous types of biofluids.

While the above is a complete description of the preferred embodiments of the invention, various alternatives, modifications and equivalents may be used. It should be evident that the present invention is equally applicable to making appropriate modifications to the embodiments described above. Therefore, the above description should not be taken as limiting the scope of the invention, which is defined by the appended claims.

What is claimed is:

1. A system for delivering a liquid sample to an inlet of an analytical instrument, the system comprising:

an acoustic ejector;

a drive system which generates drive signals for the acoustic ejector, each drive signal of the drive signals generated with a pulse width sized to generate capillary waves including a principal mound on which wave crests are formed, from which a mist of capillary droplets are emitted from the liquid sample for each drive signal;

a reservoir for holding the liquid sample, the reservoir provided in operational arrangement to the acoustic ejector;

a liquid sample voltage source designed to provide a charge to the liquid sample; and an analytical instrument voltage source in operational arrangement to the analytical instrument, designed to provide a voltage bias between the reservoir and the analytical instrument.

2. The system according to claim 1, wherein the drive system is configured to generate a pulse width below a short pulse width limit.

3. The system according to claim 1, wherein the acoustic ejector and reservoir are substantially aligned with an inlet of the analytical instrument.

4. The system according to claim 3, wherein the mist of droplets are charged to accelerate toward an inlet of the analytical instrument in a substantially direct path.

5. The system according to claim 1, further including a charge plate, having a voltage bias, the charge plate located to be in a path of the mist of droplets.

6. The system according to claim 5, wherein the inlet of the analytical instrument and the reservoir are positioned in a non-aligned relationship to each other.

7. The system according to claim 6, wherein the mist of droplets are charged to initially accelerate toward the charge plate and then be redirected to the inlet of the mass spectrometer.

8. The system according to claim 1, wherein the reservoir is a well of a multi-well well-plate.

9. The system according to claim 8, further including a protection plate or cover positioned to deter contamination of fluid in wells of the multi-well well-plate.

10. The system according to claim 1, further including a movable transport in operational arrangement to the acoustic ejector.

11. The system according to claim 8, further including a movable transport in operational attachment to the multi-well well-plate.

12. The system according to claim 1, further including a plurality of acoustic ejectors and a plurality of reservoirs, selected ones of the acoustic ejectors in operational arrangement with selected ones of the plurality of reservoirs.

13. The system according to claim 1, wherein individual droplets of the mist of droplets are sufficiently charged so as to undergo a spontaneous fission.

14. The system according to claim 1, wherein the analytical instrument is a mass spectrometer.

15. The system according to claim 1 wherein the diameter of each of the capillary droplets in the mist are of substantially the same diameter.

16. The system according to claim 1 wherein the diameter of the capillary droplets are approximately 1 micron.

17. The system according to claim 1 wherein the diameter of the capillary droplets are less than 1 micron.

18. The system according to claim 1 wherein the diameter of the capillary droplets of the mist are similar in magnitude to the capillary wavelength found by:

$$\text{wavelength}=[2*\pi*T/\rho*f^2]^{(1/3)}$$

where T is surface tension of the fluid, ρ is the density of the fluid and f is the acoustic frequency.

19. The system according to claim 1 wherein the droplets generated from the capillary wave have a mean diameter of:

$$D=0/34\ (8\pi T/\rho bf^2]^{(1/3)}$$

where T is surface tension of the fluid, ρb is the bulk liquid density of the fluid and f is the acoustic frequency.

20. The system according to claim 1 wherein the mist contains thousands of droplets generated per each drive signal, which generates an acoustic pulse.

21. The system according to claim 1, wherein the drive signal is below a minimum pulse limit, wherein drop formation is unstable.

22. The system according to claim 21 wherein the minimum pulse limit scales with the drive signal frequency, wherein as the drive frequency is increased, the minimum pulse limit is shortened.

23. A method for delivering a liquid sample to an inlet of an analytical instrument, the method comprising:

generating an acoustic drive signal, with a pulse width sized to generate capillary waves including a principal mound on which wave crests are formed, from which a mist of capillary droplets are emitted from the liquid sample;

delivering the drive signal to an acoustic ejector;

generating an acoustic wave by the acoustic ejector, based on the delivered drive signal;

directing the acoustic wave into a reservoir holding the liquid sample, wherein the acoustic wave is focused substantially at a surface of the liquid sample; and emitting a portion of the liquid sample, due to energy imparted by the acoustic signal.

24. The method according to claim 23, further including providing the liquid sample in a reservoir; and applying a charge to the liquid sample.

25. The method according to claim 24, wherein the mist of droplets carry a charge sufficient to cause spontaneous fission.

26. The method according to claim 24, wherein the droplets of the emitted mist are moved in flight by selective application of electric fields.

27. A system for delivering a liquid sample to an inlet of an analytical instrument, the system comprising:

a reservoir for holding a liquid sample;

an acoustic ejector in operational arrangement with the reservoir;

a liquid sample voltage source located within the reservoir, the liquid sample voltage source designed to provide a charge to the liquid sample; and a drive system which generates drive signals for the acoustic ejector, the drive signals generated with a pulse sized to generate capillary waves including a principal mound on which wave crests are formed, from which a mist of capillary droplets are emitted from the liquid sample for each drive signal.

* * * * *